United States Patent [19]

Shimizu et al.

[11] Patent Number: 4,704,681

[45] Date of Patent: Nov. 3, 1987

[54] ELECTROCARDIOGRAM SIGNAL PROCESSING APPARATUS FOR DETERMINING THE EXISTENCE OF THE WOLFF-PARKINSON-WHITE SYNDROME

[75] Inventors: Shigeru Shimizu; Akio Kumasaka, both of Tokyo, Japan

[73] Assignee: NEC Corporation, Tokyo, Japan

[21] Appl. No.: 724,468

[22] Filed: Apr. 18, 1985

[30] Foreign Application Priority Data

Apr. 19, 1984 [JP] Japan .................................. 59-79198

[51] Int. Cl.$^4$ ............................................ G06F 15/42
[52] U.S. Cl. .................................... 364/417; 128/704; 128/706
[58] Field of Search ................. 364/417; 128/704–706, 128/708; 33/1 C

[56] References Cited

U.S. PATENT DOCUMENTS

| | | | |
|---|---|---|---|
| 3,209,251 | 9/1965 | Edgington | 128/706 |
| 3,858,034 | 12/1974 | Anderson | 364/417 |
| 4,211,237 | 7/1980 | Nagel | 364/417 |
| 4,417,306 | 11/1983 | Citron | 364/417 |

Primary Examiner—Jerry Smith
Assistant Examiner—Gail Hayes
Attorney, Agent, or Firm—Schwartz, Jeffery, Schwaab, Mack, Blumenthal & Evans

[57] ABSTRACT

An electrocardiogram signal processing apparatus includes an analog-to-digital converter, and first, second and third processors. The analog-to-digital converter converts the input electrocardiogram signal into a digital signal. The first processor processes the digital signal by secondary differentiation to produce a secondary differentiated signal. The second processor detects the onset of the QRS complex in accordance with an input signal from the first processor, and the third processor recognizes a delta wave which is peculiar to an electrocardiogram of the Wolff-Parkinson-White syndrome in accordance with the digital signal, the secondary differentiated signal and the onset location of the QRS complex.

4 Claims, 13 Drawing Figures

FIG. 8(a)
FIG. 8(b)
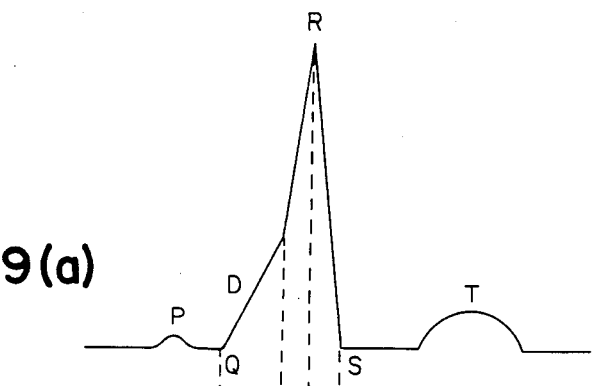
FIG. 9(a)
FIG. 9(b)

ELECTROCARDIOGRAM SIGNAL PROCESSING APPARATUS FOR DETERMINING THE EXISTENCE OF THE WOLFF-PARKINSON-WHITE SYNDROME

BACKGROUND OF THE INVENTION

The present invention relates to an electrocardiogram signal processing apparatus for automatically analyzing an electrocardiogram.

It is well known that a biological signal such as an electrocardiogram signal is analyzed by digital-processing. In such digital-processing, a analog source signal is converted into a digital signal, and smoothing and primary differential processes are performed by means of a digital filter for eliminating a noise and detecting a peak point, an onset point and an end point of a signal waveform. Consequently, characteristics of the signal waveform are extracted.

For instance, when an electrocardiogram is analyzed, a QRS complex of electrocardiogram waveforms is first detected, and on the basis of this result the respective onsets and ends of a P wave, a T wave and the QRS complex are determined, thereby measuring amplitudes and time intervals of respective waves. The thus measured values are employed as parameters for automatic analysis in relation to the electrocardiogram. Such electrocardiogram analyzes is performed by using digital filtering process which includes software.

Conduction abnormalities, especially the Wolff-Parkinson-White syndrome (hereafter called WPW syndrome) are known with respect to the electrocardiogram. The WPW syndrome electrocardiogram is characterized by having a short P-R interval (between the P onset and the Q onset), and a greater width of the QRS complex, in which a moderate slope known as the delta wave D is contained in the rising region of the R wave. In a conventional electrocardiogram analysis by using the primary differential process, it is quite difficult to accurately recognize the delta wave D, which causes low accuracy in the WPW syndrome detection.

SUMMARY OF THE INVENTION

Accordingly, it is an object of the present invention to provide an electrocardiogram signal processing apparatus which is capable of enhancing the accuracy of recognizing a delta wave in the WPW syndrome electrocardiogram signal.

According to the present invention, there is provide an electrocardiogram signal processing apparatus, comprising: an analog-to-digital converter for converting an input electrocardiogram signal into a digital signal; a first processor for processing the digital signal by secondary differentiation; a second processor for determining points of the onset and end of the QRS complex in response to the differentiated signal from the first processor; and a third processor for recognizing a delta wave D, which is peculiar to the WPW syndrome electrocardiogram, in response to the digital electrocardiogram signal, the secondary differentiated signal and the onset and end points of the QRS complex.

BRIEF DESCRIPTION OF THE DRAWINGS

FIGS. 8(a) and 8(b) respectively show the input electrocardiogram signal containing the WPW syndrome and the secondary differentiated signal;

FIGS. 9(a) and 9(b) show a schematic dominant waveform abstracted from FIGS. 9(a) and 9(b) for explaining the WPW syndrome detection.

DESCRIPTION OF THE PREFERRED EMBODIMENTS

Figures 1, 2, 4A, 4B:
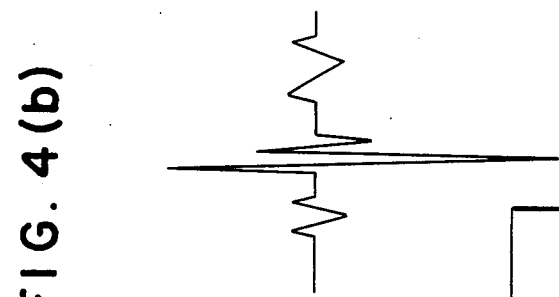
FIG. 1 shows one example of a normal electrocardiogram signal.
FIG. 2 shows an abnormal electrocardiogram signal containing a WPW syndrome.
FIGS. 4(a) and 4(b) show dominant waveforms showing an input electrocardiogram and a secondary differentiated signal, respectively.
Figure 3:
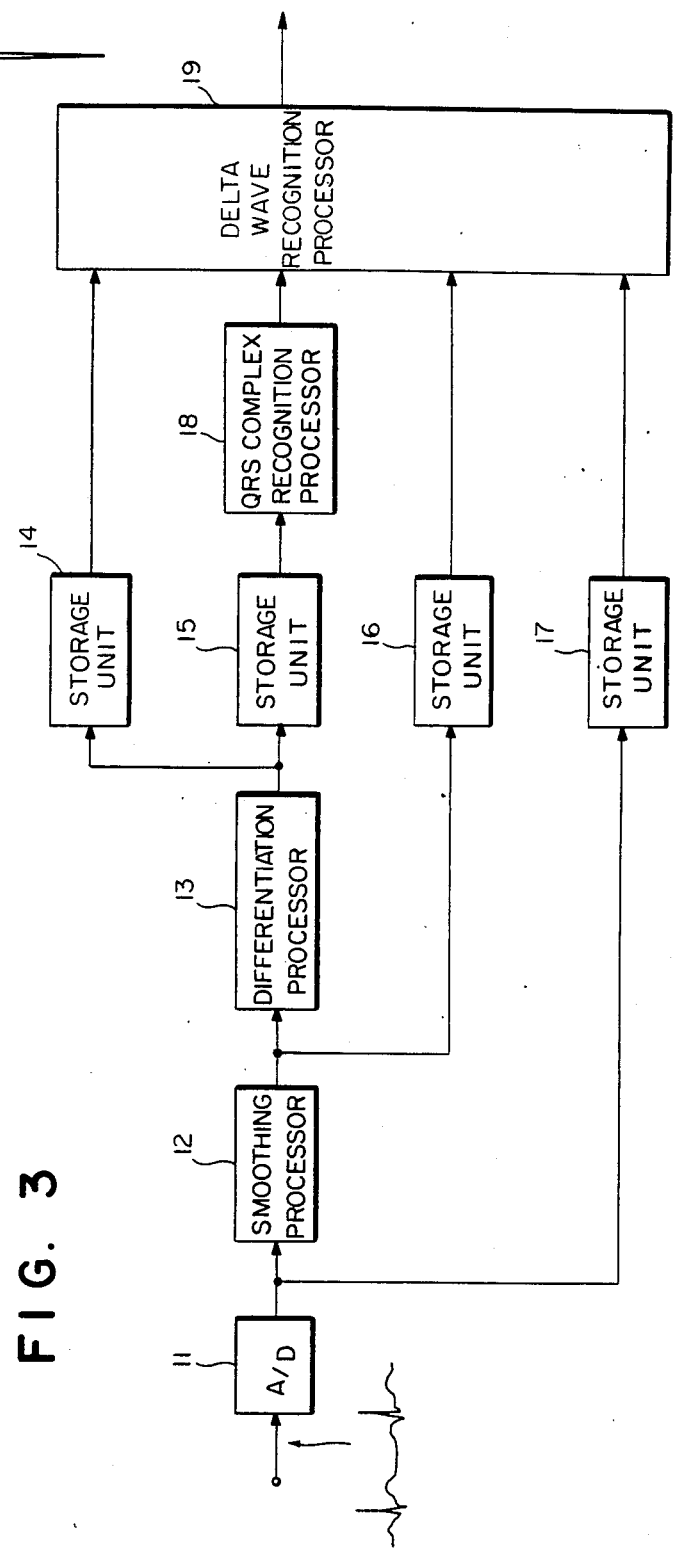
FIG. 3 shows one embodiment of the present invention.

One embodiment of the present invention will now be described in conjunction with the accompanying drawings. FIG. 1 shows one cycle of a normal electrocardiogram signal and FIG. 2 shows one cycle of abnormal electrocardiogram of the WPW syndrome. In FIG. 2, as described above, the WPW syndrome electrocardiogram signal is characterized by having a short interval between onsets of the P wave and the Q wave, and having the Delta wave D. FIG. 3 shows a schematic block diagram of one embodiment according to the present invention. In this Figure, an input electrocardiogram signal derived from an input terminal is converted into a digital signal by an analog-to-digital (A/D) converter 11 (sampling frequency: 250 Hz, resolution: 12 bit to input range of mV, for example) and is then stored in a storage unit 17. The digital signal is smoothed by a smoothing processor 12 for eliminating noise components such as electromyograms and hum or the like. The thus smoothed electrocardiogram signal is stored in a storage unit 16. Then, the smoothed signal is secondary-differentiated by a differentiation processor 13, and the secondary differentiated signal is then stored in storage units 14 and 15. A secondary differentiation filter which is employed in the differentiation processor 13 serves as a peculiar digital filter in accordance with the following formula:

$$f(T_{(k)}) = 1/T * \{ -2 \cdot (X_{(k)} + X_{(k)}) - 2 \cdot (X_{(k+1)} + X_{(k-1)}) + \quad (1)$$
$$0 \cdot (X_{(k+2)} + X_{(k-2)}) + 0 \cdot (X_{(k+3)} + X_{(k-3)}) +$$
$$1 \cdot (X_{(k+4)} + X_{(k-4)}) + 2 \cdot (X_{(k+5)} + X_{(k-5)}) +$$
$$1 (X_{(k+6)} + X_{(k-6)}) \}$$

where T represents a scale factor (constant) and $X_{(k)}$ stands for digital data of time series. As clarified in the formula (1), the digital filter makes it unnecssary to employ complicated operations in multiplication and division unlike a conventional digital fiter. The only operations needed in this digital filter are addition, subtraction and bit shift on a register, whereby high-speed processing becomes practicable. Such digital filter is disclosed in the U.S. patent application Ser. No. 560,447 "DIGITAL SIGNAL PROCESSING APPARATUS", for example. The dominant waveform of the electrocardiogram signal in shown in FIG. 4(a) and the waveform of secondary differentiated signal is shown in FIG. 4(b). The dominant waveform is, as shown in FIG. 4(a), composed of the P wave, the Q wave, the R wave, the S wave and the T wave. Further, the Q, R and S waves are treated as one unit, i.e., the QRS complex. The delta wave, which is characteristic of the WPW syndrome, is contained in the QRS complex. It is therefore necessary to initially detect the QRS complex in the smoothed signal by means of a QRS complex recognition processor 18 and, in this processor, the onset and end of the QRS complex are detected. As shown in FIG. 4(b), amplitudes of the secondary differentiated signal corresponding to the proximity of the QRS complex are greater than that corresponding to other portions. Consequently, it is relatively easy to detect the peak point since a proper threshold value has been set.

Figure 5:
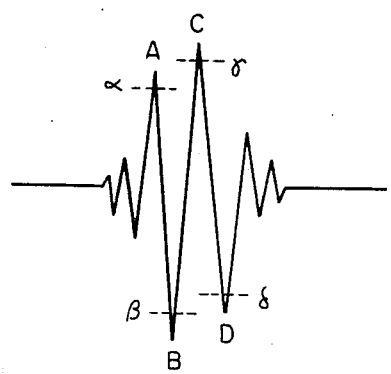
FIGS. 5 and 6 show a schematic waveform of the secondary differentiated signal for explaining a QRS complex detection process.

It is assumed that a secondary differentiated signal as shown in FIG. 5 is obtained. Threshold values $\alpha$, $\beta$, $\gamma$, $\delta$, to be employed for peak-detection are set to begin with. A negative value contained in the secondary differentiated signal is searched and, thus, a peak point B, at which the value is less than the threshold value $\beta$, is detected. After the peak point B is detected, a peak point A is searched under following conditions. The point A has the reversal polarity (the positive value) of the point B, which is more than the threshold value $\alpha$, and is previous to the point B. Thereafter, a peak point C, which is after the point B in terms of time and has a positive value, is detected. In this case, if the value of the point C exceeds the threshold value $\gamma$, this pattern of the secondary differentiated signal is deemed to a waveform of the QRS complex. When the QRS complex is recognized as described above, the time of the point B is regarded as the time of occurrence of the QRS complex, substantially. When the point A is not detected, and the point C, which exceeds the threshold value $\gamma$, is detected instead, a peak point D is detected in the vicinity thereof. In this case, if a negative value of the point D is less than the threshold value $\delta$, the point C is regarded as the time of occurrence of the QRS complex, substantially.

Figure 6:
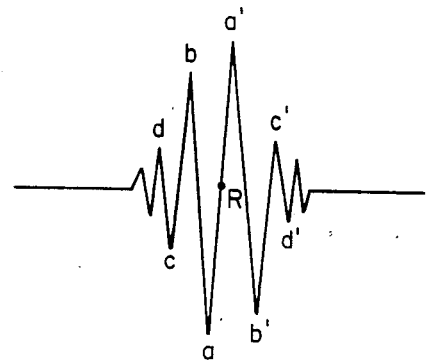
Figure 7:
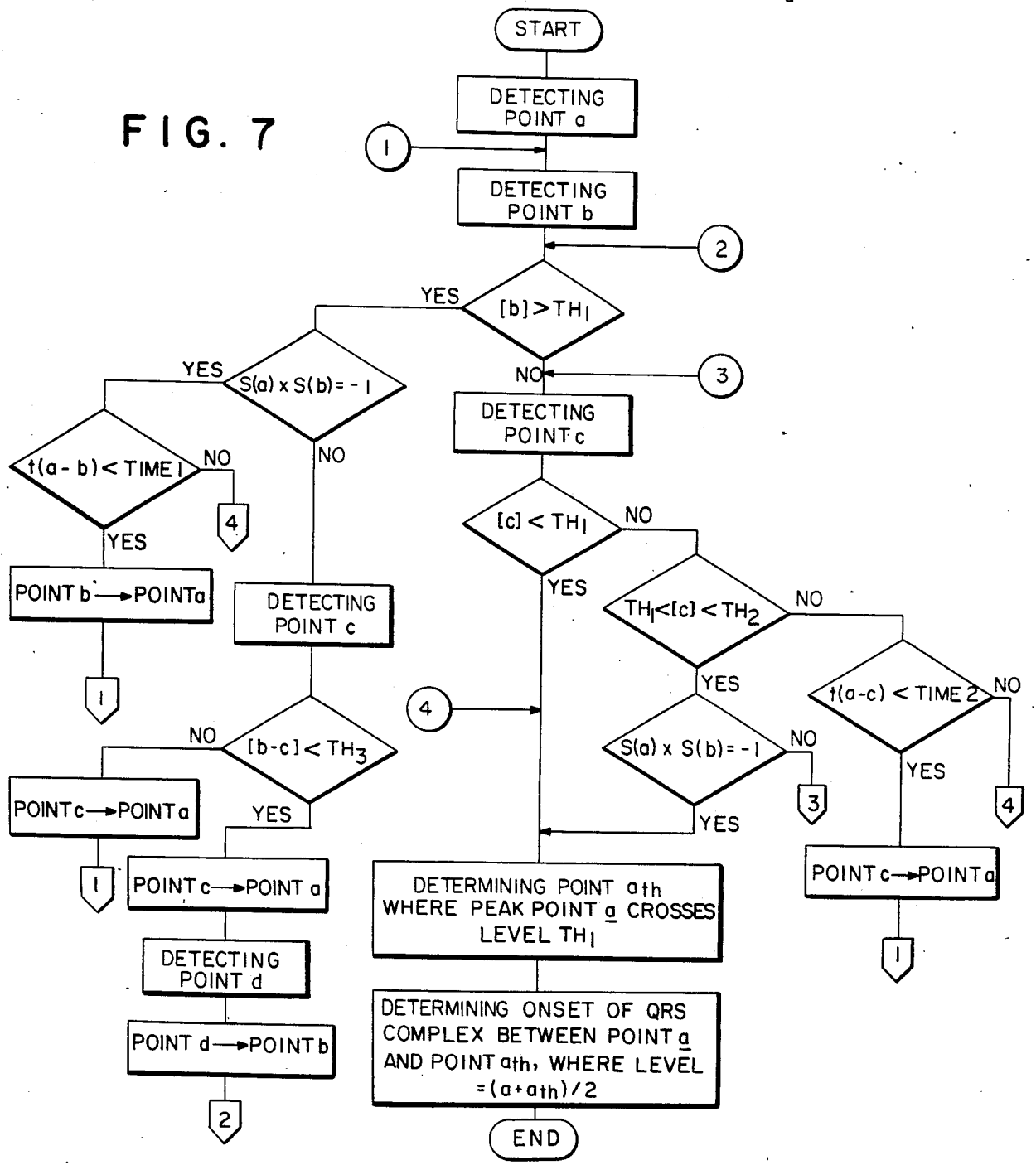
FIG. 7 shows a flowchart illustrating the process for detecting the onset of a QRS complex.

Subsequently, the onset of the QRS complex is determined. FIG. 6 shows the secondary differentiated signal in the vicinity of the QRS complex. In this Figure, it is assumed that a point R defined as an R detecting region is located between points a and a', and the peak points previous in terms of time from the point R are indicated as a, b, c and d. Similarly, the peak points which lag behind the point R are indicated as a', b', c' and d'. A detection flow with respect to the QRS onset is shown in a flow chart of FIG. 7. In the Figure, $|X|$ represents an absolute value of amplitude at a peak point X, $|X-Y|$ stands for an amplitude difference between the peak points X and Y, S(X) stands for an amplitude sign (positive: S(X)=1, negative: S(X)=−1), and t(X−Y) stands for the time difference between the peak points X and Y. Reference symbols $TH_1$, $TH_2$ and $TH_3$ respectively denote threshold values of the amplitude dimension, and Time 1, Time 2 denote threshold values of the time dimension. The end of the QRS complex can be detected by effecting the same processing as with the detection of the QRS complex onset in relation to the points a', b', c' and d' which lag behind the R detecting position in terms of time.

Figure 10:
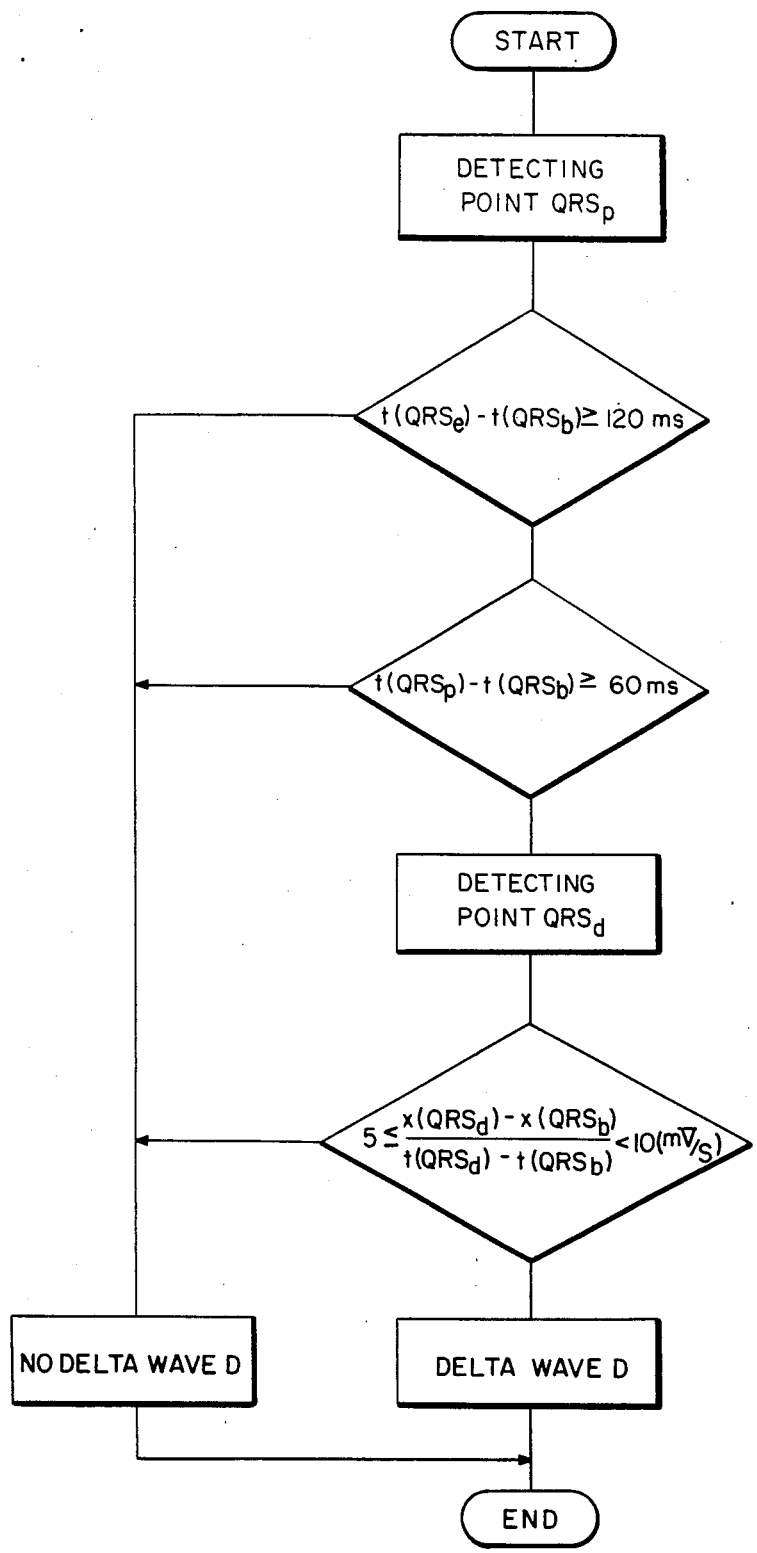
FIG. 10 shows a flowchart for detecting the WPW syndrome.

Next, the process for detecting the WPW syndrome will be described, hereinafter. The delta wave D is detected by a delta wave recognition processor 19 (FIG. 3) on the basis of the onset and end points of the QRS complex, which are detected by means of the QRS complex recognition processor 18, the smoothed electrocardiogram, and the secondary differentiated signal. The smoothed electrocardiogram signal having the WPW syndrome is shown in FIG. 8(a), and the secondary differentiated signal is shown in FIG. 8(b). FIGS. 9(a) and 9(b) schematically show dominant waveforms which are extracted from the continuous waveforms shown in FIGS. 8(a) and 8(b). The smoothed electrocardiogram signal is shown in FIG. 9(a), and the secondary differentiated signal corresponding to it is shown in FIG. 9(b). In FIG. 9(b), points $QRS_b$ and $QRS_e$ respectively stand for the QRS complex onset and its end. A point $QRS_p$ is, at first, sought under the condition that the point is between the onset of the QRS complex and the end thereof and corresponds to the peak point R of the smoothed electrocardiogram signal. So far as the WPW syndrome is concerned, the time period of the QRS complex is 120 msec or more in terms of physiology, and a ventricular activation time (corresponding to the time period between the QRS complex onset and the R wave peak point) turns out to be 60 msec or more. Therefore, a check whether or not $QRS_e - QRS_b > 120$ msec and $QRS_p - QRS_b > 60$ msec, is conducted. When the conditions are not satisfied, the corresponding symptom is judged not to be the WPW syndrome. When the conditions are satisfied, thereafter, a point $QRS_d$ is sought, under the condition that this point is between the QRS complex onset $QRS_b$ and the QRS complex peak point $QRS_p$, and it has the maximum value in regard to the secondary differentiated signal within this interval. The thus detected point is to be a candidate for the end of the delta wave D. Finally, a slope of a line segment linking the QRS complex onset with the end of the candidate point for the delta wave D is then obtained in relation to the smoothed electrocardiogram signal. The slope can be clarified according to the formula (2):

$$\frac{X(QRS_d) - X(QRS_b)}{t(QRS_d) - t(QRS_b)} \qquad (2)$$

where X(i) represents digital data (magnitude) of the smoothed electrocardiogram signal at the point i. The delta wave D slope of the WPW syndrome is considered to fall within 5 mV/second to 10 mV/second in terms of the physiology. On the basis of such reference range, discrimination whether or not the electrocardiogram signal contains the delta wave D of the WPW syndrome, is performed. FIG. 10 shows a flowchart of the WPW syndrome discriminating process. In the delta wave recognition processor 19, the digital electrocardiogram signal from the storage unit 17 may be used instead of the smoothed electrocardiogram signal from the storage unit 16.

As described above in detail, according to the present invention, it is possible to detect the WPW syndrome accurately and stably by using the secondary differentiated signal of the electrocardiogram signal.

What is claimed is:

1. An electrocardiogram signal processing apparatus comprising:
    an analog-to-digital converter for converting an input electrocardiogram signal into a digital electrocardiogram signal;

differentiation means for secondarily differentiating said digital electrocardiogram signal delivered from said analog-to-digital converter;

means for detecting a QRS complex onset on the basis of the secondary differentiated signal delivered from said differentiation means;

means for detecting an intermediate point having the maximum value, said intermediate point existing between said QRS complex onset and an R wave, in response to said secondary differentiated signal;

means for determining values of said digital electrocardiogram signal at said QRS complex onset and at said intermediate point;

means for determining a slope between said QRS complex onset and said intermediate point by using values and a distance between said QRS complex onset and said intermediate point; and means for determining the existence of the Wolff-Parkinson-White syndrome when said slope lies within a predetermined range.

2. An electrocardiogram signal processing apparatus comprising:

an analog-to-digital converter for converting an input electrocardiogram signal into a digital signal;

a first processing means for processing said digital signal by secondary differentiation to produce a secondary differentiated signal;

a second processing means for detecting an onset of the QRS complex in accordance with an output signal from said first processing means; and a third processing means for recognizing a delta wave which is peculiar to an electrocardiogram of the Wolff-Parkinson-White syndrome in accordance with said digital signal, the secondary differentiated signal delivered from said first processing means and the onset location of said QRS complex.

3. An electrocardiogram signal processing apparatus comprising:

means for converting an input electrocardiogram signal into a digital electrocardiogram signal;

means for secondarily differentiating said digital electrocardiogram signal delivered from said converting means to produce a secondary differentiated electrocardiogram signal;

means for recognizing a QRS complex contained in said input electrocardiogram signal on the basis of said secondary differentiated electrocardiogram signal to determine an onset point $QRS_b$ and an end point $QRS_e$ of said QRS complex; and means responsive to said digital electrocardiogram signal, said secondary differentiated electrocardiogram signal, said onset point $QRS_b$ and said end point $QRS_e$ for detecting a delta wave indicating the existence of the Wolff-Parkinson-White syndrome contained in said input electrocardiogram signal, wherein said delta wave detecting means includes:

means for detecting a point $QRS_p$ corresponding to a peak point between said onset point $QRS_b$ and said end point $QRS_e$;

means for detecting a point $QRS_d$ between said onset point $QRS_b$ and said point $QRS_p$, said point $QRS_d$ having the maximum value in regard to said secondary differentiated signal within the interval between said onset point $QRS_b$ and said point $QRS_p$;

means for calculating a value of $$\frac{X(QRS_d) - X(QRS_b)}{t(QRS_d) - t(QRS_b)},$$

said $X(QRS_d)$ indicating a value of said digital electrocardiogram signal at said point $QRS_d$, said $X(QRS_b)$ indicating a value of said digital electrocardiogram signal at said onset point $QRS_b$ and said $\{t(QRS_d)-t(QRS_B)\}$ indicating said interval between said onset point $QRS_b$ and said point $QRS_d$, and;

means for determining the presence of said delta wave in said input electrocardiogram signal when said value of $$\frac{X(QRS_d) - X(QRS_b)}{t(QRS_d) - t(QRS_b)}$$

lies in a predetermined range.

4. An electrocardiogram signal processing method comprising:

converting an input electrocardiogram signal into a digital electrocardiogram signal;

secondarily differentiating said digital electrocardiogram signal to produce a secondary differentiated electrocardiogram signal;

detecting a QRS complex onset point $QRS_b$ and a QRS complex end point $QRS_e$ on the basis of said secondary differentiated electrocardiogram signal;

detecting an R wave point $QRS_p$ between said QRS complex onset point $QRS_b$ and said QRS complex end point $QRS_e$, said R wave point $QRS_p$ corresponding to a peak point between said QRS complex onset point $QRS_b$ and said QRS complex end point $QRS_e$;

detecting a point $QRS_d$ under the condition that said point $QRS_d$ is between said QRS complex onset point $QRS_b$ and said R wave point $QRS_p$ and has the maximum value in regard to said secondary differentiated signal within the interval between said QRS complex onset point $QRS_b$ and said R wave point $QRS_p$;

determining a condition that the interval $\{t(QRS_e)-t(QRS_b)\}$ between said QRS complex onset point $QRS_b$ and said QRS complex end point $QRS_e$ is greater than a first predetermined period and the interval $\{t(QRS_p)-t(QRS_b)\}$ between said R wave point $QRS_p$ and said QRS complex onset point $QRS_b$ is greater than a second predetermined period;

calculating a value of $$\frac{X(QRS_d) - X(QRS_b)}{t(QRS_d) - t(QRS_b)},$$

said $X(QRS_d)$ corresponding to a magnitude of said input electrocardiogram signal at said point $QRS_d$, said $X(QRS_b)$ corresponding to a magnitude of said input electrocardiogram signal at said QRS complex onset point $QRS_b$ and said $\{t(QRS_d)-t(QRS_b)\}$ corresponding to the interval between said point $QRS_d$ and said QRS complex onset point $QRS_b$; and determining the existence of said Wolff-Parkinson-White syndrome under said condition detected by determining the step when said value of $$\frac{X(QRS_d) - X(QRS_b)}{t(QRS_d) - t(QRS_b)}$$

lies within a predetermined range.

* * * * *